United States Patent
Fukuda et al.

[11] Patent Number: 5,908,826
[45] Date of Patent: Jun. 1, 1999

[54] FREEZE-DRIED PREPARATION CONTAINING MONOCLONAL ANTIBODY

[75] Inventors: Tamotsu Fukuda; Yukio Shimazaki; Yasuyuki Kuroiwa; Shiro Takagi, all of Mobara, Japan

[73] Assignee: Mitsui Toatsu Chemicals Inc., Japan

[21] Appl. No.: 08/340,319

[22] Filed: Nov. 14, 1994

Related U.S. Application Data

[63] Continuation of application No. 07/940,970, Nov. 5, 1992, abandoned, which is a continuation of application No. PCT/JP92/00226, Feb. 28, 1992.

[30] Foreign Application Priority Data

Mar. 8, 1991 [JP] Japan ...................................... 3-43431

[51] Int. Cl.⁶ .......................... C07K 16/00; A61K 39/395
[52] U.S. Cl. ........................ 514/8; 424/142.1; 530/388.1; 530/388.15
[58] Field of Search ........................... 530/388.1, 388.15; 514/8; 424/142.1

[56] References Cited

FOREIGN PATENT DOCUMENTS

| | | |
|---|---|---|
| 0 140 489 | 5/1985 | European Pat. Off. . |
| 0 177 836 | 4/1986 | European Pat. Off. . |
| 0 190 041 | 8/1986 | European Pat. Off. . |
| 57-140724 | 8/1982 | Japan . |
| 58-167518 | 10/1983 | Japan . |
| 60-146833 | 8/1985 | Japan . |
| 60-248626 | 12/1985 | Japan . |
| 61-76423 | 4/1986 | Japan . |
| 61-78730 | 4/1986 | Japan . |
| 61-78731 | 4/1986 | Japan . |
| 61-191622 | 8/1986 | Japan . |
| 61-194035 | 8/1986 | Japan . |
| 62-292731 | 12/1987 | Japan . |
| 63-88197 | 4/1988 | Japan . |
| WO 89/11297 | 11/1989 | Japan . |
| 2-493 | 1/1990 | Japan . |
| WO 90/11350 | 10/1990 | Japan . |
| 3-504499 | 10/1991 | Japan . |
| 700132 | 11/1979 | U.S.S.R. . |
| WO 88/04669 | 6/1988 | WIPO . |
| 8911298 | 11/1989 | WIPO . |
| WO 90/11091 | 10/1990 | WIPO . |

OTHER PUBLICATIONS

Azrin M.A., *American Heart Journal,* vol. 124(3), pp. 753–768 (1992)); specifically in the section "Summary," left column on page 766.

Katus. et al., *Circulation Abstracts,* vol. 68(4), p. III–80 (1983).

O'oka, H. et al., *Microbial. Immunol.,* vol. 36(12), pp. 1305–1316 (1992) specifically in line 11–19, pp. 1314, line 4–1 from the bottom of the same page, and line 3–7, pp. 1315.

Chemical Abstract 101. 53015μ (1984)—Chemical Abstract of SU 700132.

Vox Sang. 51:81–86 (1986) Tomeno et al. "A New Intact Immunoglobulin for Intravenous Use Stabilized by Chemically Modified Gelatin Derivatives" pp. 81–86.

Borrebaeck, Journal of Immunological Methods, vol. 123 pp. 157–165 (1989).

Waldmann, Science, vol. 252, pp. 1657–1662 (1991).

Spalding, Bio/Technology, vol. 11, pp. 428–429 (1993).

*Primary Examiner*—Frank C. Eisenschenk
*Attorney, Agent, or Firm*—Nixon & Vanderhye

[57] ABSTRACT

A freeze-dried monoclonal antibody preparation is prepared by adding to a solution of the monoclonal antibody gelatin or carboxylic acid or its salt, to prevent denaturation of the monoclonal antibodies during freeze-drying. Freeze-dried monoclonal antibody preparations having stablized antigen-binding activity result and may be used as an adminiculum for immunoauxotherapy for prophylaxis and treatment of bacterial infectious diseases and viral infectious diseases.

5 Claims, No Drawings

FREEZE-DRIED PREPARATION CONTAINING MONOCLONAL ANTIBODY

This is a continuation of application Ser. No. 07/940,970, filed Nov. 5, 1992, now abandoned which is a continuation of PCT/JP92/00226 Feb. 28, 1992.

FIELD OF THE INVENTION

The present invention relates to a freeze-dried preparation comprising a monoclonal antibody(or antibodies) as a main ingredient(s).

PRIOR ART

A monoclonal antibody is a homogeneous globulin protein having reactivity to only a specific epitope. Recent progress in technologies of cell fusion, cultivation and protein purification, etc. has made it possible to produce large amounts of monoclonal antibodies. As a result, monoclonal antibodies have come to be utilized in various fields, such as various analyses, diagnoses, treatments and prophylaxes. In particular, expectations of monoclonal antibodies as medicines for treatments and prophylaxes are increasing. Above all, their application to humans is expected to be developed further in future, and development of human-derived monoclonal antibodies which are favorable in point of antigenicity is being advanced.

Hitherto, in this technical field, polyclonal antibodies such as immunoglobulin preparations have been used for the same purpose for medical diagnosis and treatment. While a monoclonal antibody is a homogeneous one having reactivity to only a specific epitope, a polyclonal antibody is a mixture of plural antibodies as is named so. Therefore, in a polyclonal antibody, plural molecules each having different properties act to mutually stabilize them so that such a polyclonal antibody is, as a whole, in a relatively stable state. However, in a purified monoclonal antibody, stabilization by the interaction between different molecules could not be expected so that such a monoclonal antibody is unstable to various physical and chemical actions irrespective of the immunoglobulin class of itself.

Globulin proteins such as monoclonal antibodies and polyclonal antibodies are often heated for the purpose of inactivating viruses therein, especially when they are used for medical diagnosis and treatment. Such globulin proteins are unsuitable to storage in the solutions for a long period of time. Therefore, employment of freeze-drying has been common for a stable storage of such globulin protein molecules. In addition, the globulin proteins are often treated with acids or alkali substances, if desired.

To such heat-treatment, freeze-drying and acid- or alkali-treatment, polyclonal antibodies are generally stable, but monoclonal antibodies would often be denatured and easily lose their activity by such treatment. In particular, IgM is less stable than any other monoclonal antibodies of other immunoglobulin classes (e.g., IgG, IgA and IgE). Regarding heat-treatment of antibodies, for example, JP-A 61-76423 (the term "JP-A" means an "unexamined published Japanese patent application") discloses the fact that monoclonal antibodies are unstable to heat-treatment and that, for the purpose of overcoming thermal instability, a hydrolysate of ovalbumin is added to a monoclonal antibody preparation.

On the other hand, freeze-drying treatment involves a problem specific to monoclonal antibodies. Namely, in freeze-drying a monoclonal antibody, if a monoclonal antibody solution is freeze-dried without adding a stabilizer thereto, there occurs a problem of decrease of the antigen-binding activity of the monoclonal antibody due to denaturation of itself during freeze-drying. Therefore, it is necessary to prevent this problem. The problem is noticeable in freeze-drying a monoclonal antibody, while it is not so significant in freeze-drying a polyclonal antibody as a polyclonal antibody is stable because of the above-mentioned reasons.

In preparing a freeze-dried product of a monoclonal antibody, addition of albumin of a heterologous protein to a solution of a monoclonal antibody before freeze-drying (for example, JP-A 60-146833, 61-78730 and 61-78731, and WO 90/11091) or addition of maltose of a saccharide thereto) (for example, WO 89/11297) is known.

Immunoglobulin praparations of polyclonal antibodies are usually used at a relatively high concentration, and aggregates would often form in the solutions during storage or during the succeeding freeze-drying treatment. The aggregates are considered to cause a serious anaphylactoid side effect, when the globulin containing them is intravenously injected to human bodies. Therefore, for the purpose of preventing formation of such aggregates, addition of a heterologous protein to the stock solutions is known. For instance, addition of gelatin alone of a heterologous protein to an immunoglobulin solution (for example, JP-A 58-167518, vox.) Sang. (1983) 51, 81–86) or addition of both sucrose of a saccharide and gelatin thereto is known to be effective for preventing formation of aggregates in the stock solutions and also for maintaining antibacterial and antiviral activities (SU 700132). All the technologies as disclosed above are to prevent formation of aggregates in a high concentration solution of an immunoglobulin of a polyclonal antibody. None of them mention or discuss the matter of decrease of the antigen-binding activity of polyclonal antibodies due to the freeze-drying treatment. On the other hand, a monoclonal antibody is stored or freeze-dried in the form having a relatively low concentration. Even under such a low concentration, however, there is still a problem of denaturation of a monoclonal antibody during freeze-drying as well as a problem of decrease of its antigen-binding activity. The matter has not heretofore been identified as to whether or not addition of gelatin used to prevent formation of aggregates of immunoglobulins would be useful for solving this problem.

On the other hand, it is widely known that carboxylic acids and their salts are used as a component of buffers for pH maintenance of various protein solutions. For instance, WO 89/11298 discloses the addition of maltose, sodium chloride or sodium phosphate, as a stabilizer, to a stock solution of a monoclonal antibody for the purpose of preventing formation of aggregates which precipitate in the solution. It also mentions use of sodium citrate, instead of sodium phosphate, as a component of the buffer. However, it merely indicates a technique of preventing formation of aggregates in a stock solution of a monoclonal antibody during storage, but it does not disclose a treatment for freeze-drying a monoclonal antibody, a treatment for preventing denaturation of a monoclonal antibody during freeze-drying it and also a treatment for preventing decrease of the antigen-binding activity thereof. WO 89/11297 discloses a technique of adding maltose, as a stabilizer, to a monoclonal IgG antibody solution to be freeze-dried and further adding, as a buffer component, 5 to 10 mM sodium acetate thereto so that the pH value of the solution is kept within an acidic range of being from 3 to 6. In this case, sodium acetate is obviously used as a component of a buffer solution. WO 89/11297 suggests nothing as to the fact that carboxylic acid or its salt would still act as a stabilizer for preventing denaturation of antibody during freeze-drying treatment thereof in the pH range where the carboxylic acid or its salt does not exert a buffer action. Regarding a pH range of an antibody solution, if an antibody solution having a low pH value is intravenously injected pain or injection often occurs. Where an antibody solution is used as an injection, it is desirable to have a pH value in an approximately neutral pH range. However, utilization of such an antibody solution in a neutral pH range is not suggested in WO 89/11297.

For the purpose-of inactivating viruses which could contaminate immunoglobulins in preparing them from sera or plasma, immunoglobulins are often heated in the form of their solutions. For instance, JP-A 62-292731, 61-194035, 61-191622 and 57-140724 disclose the addition of carboxylic acids to said globulin solutions for this purpose. JP-A 61-78730 and 61-78731 disclose the addition of sodium acetate to immunoglobulin preparations and heating them in a dry state. However, all of them merely mention the addition of carboxylic acids for the purpose of stabilizing immunoglobulin preparations in the heat-treatment. It has not heretofor been known whether or not carboxylic acids and their salts would be useful for preventing denaturation of antibodies during freeze-drying and also for preventing a decrease of their antigen-binding activity owing to said denaturation.

PROBlEM TO BE SOLVED BY THE INVENTION

The object of the present invention is to provide stable freeze-dried preparations of monoclonal antibodies, which are free from denaturation of the monoclonal antibodies during freeze-drying and from a decrease of their antigen-binding activity owing to said denaturation.

MEANS FOR SOLVING THE PROBLEM

The present inventor shave found that gelatin, carboxylic acids or their salts are effective for stabilizing a monoclonal antibody in freeze-drying it. Namely, they have found that, by addition of gelatin to a solution containing a monoclonal antibody to be freeze-dried, denaturation of the monoclonal antibody during freeze-drying as well as decrease of its antigen-binding activity may be prevented and that, by the addition of carboxylic acid or its salt to a solution containing a monoclonal antibody to be freeze-dried, denaturation of the monoclonal antibody during freeze-drying as well as decrease of its antigen-binding activity owing to said denaturation may be prevented over a broad pH range and even at a pH value being outside the range where a buffer action is exhibited. On the basis of these observations, applicants have found that it is possible to prepare a stable and highly safe preparation of a monoclonal antibody.

Specifically, the present invention provides a freeze-dried preparation containing a monoclonal antibody and geltain as well as a preparation prepared by freeze-drying a solution containing a monoclonal antibody and carboxylic acid or its salt and having pH between 6.1 and 8.1.

The monoclonal antibody to be used in the present invention may be any monoclonal antibody that is generally obtained from human beings, mice, rats and others, and the origins and the producing means are not specifically defined. For instance, the monoclonal antibody for use in the present invention may be obtained from a culture supernatant as obtained by cultivating antibody-producing cells as prepared by known methods such as a cell fusion method or a transformation method, or by cultivating cells into which a cloned antibody gene has been incorporated, or from ascites, etc. of a mouse into which such antibody-producing cells have been transplanted. For purifying the monoclonal antibody obtained from such a cell culture supernatant or mouse ascites or the like, usable are various purification methods such as ammonium sulfate salting-out, ion exchange chromatography, gel filtration, affinity chromatography, ultra-centrifugation, adsorption chromatography and hydrophobic chromatography. The immunoglobulin classes of the monoclonal antibody to be used in the present invention are mostly IgG, IgM, IgA and IgE, but they are not specifically defined. A monoclonal antibody of any immunoglobulin class can be used in the present invention. Above all, IgM is less stable than those of other immunoglobulin classes. Therefore, the stabilizing method effective for the IgM class monoclonal antibody may easily be applied to monoclonal antibodies of other immunoglobulin classes. In fhe present invention, a single monoclonal antibody may be used or several monoclonal antibodies may be also used as a mixture of them with no problem.

Gelatin may be grouped into two types (neutral type and acidic type) according to the methods of preparing it, of which the isoelectric points are different from each other. Both of them may be used in the present invention. In addition, chemically modified gelatins such as oxypolygelatin or modified liquid gelatins may be also used.

As carboxylic acid, usable are, for example, citric acid, acetic acid, oxalic acid, succinic acid and fumaric acid. Citric acid is preferable. As salt of carboxylic acid, usable are, for example, sodium citrate, potassium citrate, sodium acetate, potassium acetate, sodium oxalate, potassium oxalate, sodium succinate, potassium succinate, sodium fumarate and potassium fumarate. Sodium citrate is preferable.

For the purpose of stabilizing the monoclonal antibody or for the purpose of pH adjusting, isotonicating and buffering the monoclonal antibody-containing solution to be freeze-dried, inorganic salt, monosaccharide, disaccharide, sugar alcohol or amino acid may be further added, in addition to gelatin or carboxylic acid or its salt.

As inorganic salt, usable are, for example, sodium chloride, potassium chloride and magnesium chloride. Sodium chloride is preferable.

As monosaccharide, usable are, for example, glucose, mannose, galactose and fructose. Glucose or mannose is preferable.

As disaccharide, usable are, for example, maltose, sucrose and lactose. Maltose or sucrose is preferable.

As sugar alcohol, usable are, for example, sorbitol and mannitol. Mannitol is preferable.

As amino acid, usable are, for example, glycine, alanine, valine, leucine, isoleucine, tyrosine, phenylalanine, serine, threonine, glutamine, glutamic acid, asparagine, aspartic acid, arginine, lysine, histidine, proline, tryptophan, methionine and cysteine. Glycine or arginine is preferable.

For producing the freeze-dried preparation of the present invention, a monoclonal antibody solution containing gelatin or carboxylic acid or its salt may be freeze-dried. Preferably, the monoclonal antibody solution is added to a buffer containing gelatin or carboxylic acid or its salt having an adjusted pH value; or gelatin or carboxylic acid or its salt is added to a monoclonal antibody-containing solution. The concentration of the monoclonal antibody in the solution to be used in the present invention is from 0.01 mg/ml to 50 mg/ml, preferably from 0.1 mg/ml to 10 mg/ml. The amount of gelatin is from 1/100 to 100 parts by weight to one part by weight of the monoclonal antibody. Preferably, it is from 1/10 to 10 parts by weight to one part by weight of the same. The concentration of carboxylic acid or its salt to be added is from 2 mmoto 500 mM, preferably from 10 mM to 200 mM.

The pH value of the solution for dissolving the monoclonal antibody to be freeze-dried is from 4.0 to 8.1 when gelatin is added thereto; or it is from 6.1 to 8.1, preferably from 6.5 to 7.8, when carboxylic acid is added or both gelatin and carboxylic acid are added. Adjustment of the pH value of the solution may be done using organic acids, inorganic acids, inorganic salts or other compounds which are generally used for pH adjustment, singly or in combination of two or more of them. As a compound usable for such pH adjustment, there are mentioned, for example, citric acid, sodium citrate, potassium citrate, phosphoric acid, sodium phosphate, potassium phosphate, hydrochloric acid, tris(hydroxymethyl)aminomethane, acetic acid, sodium acetate, potassium acetate, sodium hydroxide, boric acid, sodium borate, and potassium borate. The concentration of the buffer solution for dissolving the monoclonal antibody is from 5 mM to 500 mM, preferably from 10 mM to 500 mM. As mentioned above, carboxylic acid or its salt may be also used for pH adjustment of a monoclonal antibody containing solution, and the above-mentioned amount of the acid or its salt indicates the total amount thereof in the solution including the amount for pH adjustment.

The thus prepared monoclonal antibody solution may be stable when freeze-dried directly as it is. It is also possible to add thereto a surfactant such as TWEEN 20 or TWEEN 80, a human or bovine albumin, or a chelating agent such as EDTA, for the purpose of isotonicating the solution or of preventing adhesion of the monoclonal antibody to the container containing the solution.

Freeze-drying of the monoclonal antibody solution may be carried out by any ordinary known method, and the drying temperature and the vacuum degree in the method may be selected suitably.

EXAMPLES

Next, the present invention will be explained by way of the following examples, which are, however, not limitative. IgM is exemplified herein as a monoclonal antibody in the present invention. This is because, as mentioned above, IgM is less stable than antibodies of other immunoglobulin classes (e.g., IgG, IgA and IgE), and therefore the stabilizing effect to be verified in IgM may be easily applied to antibodies of other immunoglobulin classes.

Example 1

Cells of Epstein-Barr virus (EB virus) transformed cell line MP-5038 (FERM BP-1596) producing an IgM antibody reactive to Group E serotype *Pseudomonas aeruginosa* were cultured, and a human monoclonal antibody was purified from the culture supernatant by ammonium sulfate salting-out, gel filtration with SEPHACRYL S-300 (Pharmacia Co.) and column chromatography with a hydroxyapatite HPLC column (Mitsui Toatsu Chemicals, Inc.) and BLUE-SEPHAROSE (Pharmacia Co.). The monoclonal antibody as obtained by these methods had a purity of 99% or higher, as analyzed by SDS-polyacrylamide gel eletrophoresis and HPLC with a gel filtration column. The monoclonal antibody was dissolved in a phosphate-buffered physiological saline having an adjusted pH value of 7.4 (hereinafter referred to as PBS), to have a final concentration of 0.1 mg/ml. On the other hand, gelatin (high-grade gelatin; Nippi Co., type A (neutral gelatin) and type B (acidic gelatin)) was added thereto to have a final concentration of 0.001 to 1%. The resulting solution was then put in 2 ml-volume polypropylene cryotubes (Corning Co.) under a sterilized condition, each in an amount of 0.5 ml, and frozen therein at −80° C. These were freeze-dried in vacuo. After drying, the same amount, as that before freeze-drying, of a distilled water for injection was added to the freeze-dried product so that the product was dissolved. The antigen-binding activity of the monoclonal antibody in the resulting solution was measured.

Measurement of the antigen-binding activity of the anti-*Pseudomonas aeruginosa* antibody was carried in the manner mentioned below. A lipopolysaccharide (LPS), as prepared from formalin-killed cells of Group E serotype *Pseudomonas aeruginosa* ATCC 27581 by Tanabe et al's method (Menekijikkensousahou C, (1978) 1793–1801), was dissolved in PBS to have a concentration of 1 mg/ml, and this was diluted by 500-fold with 0.1M phosphate buffer (pH 7.0). The thus diluted solution was then put in wells of a 96-well EIA plate (Immulon-600; Greiner Co.) in an amount of 50 $\mu$l/well. The plate was allowed to stand at 4° C. overnight for coating, and it was then washed with PBS containing 0.05% TWEEN 20 (hereinafter referred to as a "washing solution"). A PBS containing 0.5% bovine serum albumin (hereinafter referred to as a "blocking solution") was added to each well in an amount of 200 $\mu$l/well, and the plate was then shaken at room temperature for one hour so that the non-specific protein-binding sites were saturated. After the blocking solution was removed, solutions of a sample to be tested, each having a multi-fold diluted concentration in order from a determined concentration, were put in the wells each in an amount of 100 $\mu$l/well, and the plate was then shaken for 2 hours at room temperature. After washing with the washing solution four times, a peroxidase-labeled goat anti-human IgM antibody (Tago Co.) was diluted by 1000-fold with the blocking solution, and was put in each well in an amount of 100 $\mu$l/well, and the plate was shaken at room temperature for 2 hours. After washing with the washing solution four times and then with 0.1M citric-acid buffer (pH 4.0) one time, a substrate solution containing 1 mg/ml of 2,2'-azinobis(3-ethylbenzothiazoline-6-sulfonic acid) and 0.003% hydrogen peroxide in the same buffer was put into each well in an amount of 50 $\mu$l/well, and the plate was then shaken at room temperature. After 30 minutes, 2% succinic acid was added to each well in an amount of 50 $\mu$l/well so that the enzymatic reaction therein was stopped. The absorbance at 414 nm was measured with a 96-well plate reader (Nippon InterMed Co.). Double logarithmic plotting was done between the reciprocal of the diluting magnification and the absorbance, and the diluting magnification to show the absorbance of being 0.1 was obtained and indicated as the antigen-binding activity of the sample tested.

The results are shown in Table 1, as a relative activity on the basis of the antigen-binding activity of the sample before being frozen of 10.Where the monoclonal antibody was freeze-dried without addition of gelatin thereto, the antigen-binding activity noticeably decreased. As opposed to the case, when gelatin was added, the antigen-binding activity was well recovered even in the freeze-dried product, and the effect depended upon the concentration of the gelatin added.

TABLE 1

| Gelatin Concentration | Antigen-Binding Activity | |
|---|---|---|
| (%) | Neutral Gelatin | Acidic Gelatin |
| 0 | 2 | 2 |
| 0.001 | 4 | 3 |
| 0.003 | 6 | 6 |
| 0.01 | 10 | 8 |
| 0.03 | 10 | 10 |
| 0.1 | 10 | 10 |
| 1 | 10 | 10 |

Example 2

The same monoclonal antibody as that used in Example 1 was dissolved in various buffers each having a different pH value to each have a final concentration of 0.1 mg/ml. On the other hand, a neutral gelatin was added to each of them to have a final concentration of 0.01%. Each was put in polypropylene cryotubes each in an amount of 0.5 ml under a sterilized condition and frozen at −80° C. These were then freeze-dried in vacuo. The same amount, as that before freeze-drying, of a distilled water for injection was added to the freeze-dried product so that the product was dissolved, and the antigen-binding activity of the monoclonal antibody in the resulting solution was measured.

The results obtained are shown in Table 2, as a relative activity based on the activity of the sample before being frozen of 10. At every pH condition, the antigen-binding activity was well recovered.

TABLE 2

| Buffer (0.2M) | pH | Gelatin Concentration (%) | Antigen-Binding Activity |
|---|---|---|---|
| Sodium Citrate | 4.0 | 0.01 | 10 |
|  | 5.0 | 0.01 | 10 |
|  | 6.0 | 0.01 | 10 |
| Sodium Phosphate | 6.2 | 0.01 | 10 |
|  | 7.0 | 0.01 | 10 |
|  | 8.1 | 0.01 | 10 |

Example 3

0.1 mg,ml, as a final concentration, of the same monoclonal antibody as that used in Example 1 was dissolved in 20 mM phosphate buffer (pH 7) not containing or containing 2 or 10 mM sodium citrate, whereupon the salt concentration of the resulting solution was adjusted to be 150 mM with sodium chloride. The monoclonal antibody solution was then put in polypropylene cryotubes under sterile conditions, each in an amount of 0.5 ml, and frozen therein at −80° C. These were freeze-dried in vacuo. The same amount, as that before freeze-drying, of a distilled water for injection was added to the freeze-dried product so that the product was dissolved. The antigen-binding activity of the monoclonal antibody in the resulting solution was measured.

The results obtained are shown in Table 3, as a relative activity based on the activity of the sample before being frozen of 10. Where the monoclonal antibody was freeze-dried in the absence of sodium citrate, the antigen-binding activity of the freeze-dried monoclonal antibody noticeably decreased. As opposed to the case, when the monoclonal antibody was freeze-dried in the presence of sodium citrate, then the antigen-dinding activity of the freeze-dried monoclonal antibody was well recovered, depending upon the concentration of the sodium citrate added.

TABLE 3

| Sodium Citrate Concentration (mM) | 0 | 2 | 10 |
|---|---|---|---|
| Antigen-Binding Activity | 2 | 5 | 9 |

Example 4

0.1 mg/ml, as a final concentration, of the same monoclonal antibody as that used in Example 1 was dissolved in 50 mM phosphate buffer (pH 6.1 to 8.1) containing sodium citrate in a concentration of from 10 mM to 200 mM, whereupon sodium chloride was added thereto, if necessary, so that the salt concentration of the resulting solution became 160 mM. The resulting monoclonal antibody solution was then put in polypropylene cryotubes under a sterilized condition, each in an amount of 0.5 ml, and frozen therein at −80° C. These were freeze-dried in vaccuo. The same amount, as that before freeze-drying, of a distilled water for injection was added to the freeze-dried product so that the product was dissolved. The antigen-binding activity of the monoclonal antibody in the resulting solution was measured.

The results obtained are shown in Table 4, as a relative activity based on the activity of the sample before being frozen of 10. By adding sodium citrate at pH of from 6.1 to 8.1, the antigen-binding activity of all the freeze-dried products was well recovered.

TABLE 4

| pH of Solution | Antigen-Binding Activity Sodium Citrate Concentration (mM) | | | |
|---|---|---|---|---|
|  | 10 | 50 | 100 | 200 |
| 6.1 | 10 | 10 | 10 | 10 |
| 7.0 | 9 | 10 | 10 | 10 |
| 8.1 | 9 | 10 | 10 | — |

Example 5

0.1 mg/ml, as a final concentration, of the same monoclonal antibody as that used in Example 1 was dissolved in PBS. In addition, 0.003%, as a final concentration, of a neutral gelatin was added thereto, and further glucose, sucrose, mannitol, glycine or arginine was added thereto in an amount, as a final concentration, of from 0.001 to 0.1%. The resulting monoclonal antibody solution was then put in polypropylene cryotubes under a sterilized condition, each in an amount of 0.5 ml, and frozen therein at −80° C. These were freeze-dried in vacuo. The same amount, as that before freeze-drying, of a distilled water for injection was added to the freeze-dried product so that the product was dissolved. The antigen-binding activity of the monoclonal antibody in the resulting solution was measured.

The results obtained are shown in Table 5, as a relative activity based on the activity of the sample before being frozen of 10. The antibody activity was well recovered in all cases of the low molecular substances, depending upon the concentration of them.

TABLE 5

| Concentration of Gelatin (%) | Concentration of Low Molecular Substance (%) | Antigen-Binding Activity | | | | |
|---|---|---|---|---|---|---|
| | | glucose | sucrose | mannitol | glycine | arginine |
| 0.003 | 0.001 | 7 | 7 | 7 | 8 | 7 |
| 0.003 | 0.003 | 8 | 8 | 7 | 8 | 8 |
| 0.003 | 0.01 | 8 | 6 | 8 | 10 | 8 |
| 0.003 | 0.03 | 8 | 8 | 8 | 10 | 8 |
| 0.003 | 0.1 | 8 | 10 | 8 | 10 | 8 |
| 0.003 | 0 | 6 | 6 | 6 | 6 | 6 |

Example 6

0.1 mg/ml, as a final concentration, of the same monoclonal antibody as that used in Example 1 was dissolved in PBS. In addition, 0.003%, as a final concentration, of a neutral gelatin was added thereto, and further 0.5 or 1%, as a final concentration, of mannitol was added thereto. The resulting monoclonal antibody solution was then put in polypropylene cryotubes under a sterilized condition, each in an amount of 0.5 ml, and frozen therein at −80° C. These were freeze-dried in vacuo. The same amount, as that before freeze-drying, of a distilled water for injection was added to the freeze-dried product so that the product was dissolved. The antigen-binding activity of the monoclonal antibody in the resulting solution was measured.

The results obtained are shown in Table 6, as a relative activity based on the activity of the sample before being frozen of 10. The antigen-binding activity was well recovered in all the freeze-dried products, each containing a different concentration of mannitol.

TABLE 6

| Concentration of Mannitol (%) | 0.5 | 1.0 |
|---|---|---|
| Antigen-Binding Activity | 10 | 10 |

Example 7

1 mg/ml, as a final concentration, of the same monoclonal antibody as that used in Example 1 was dissolved in 0.1M phosphate buffer (pH 7.0) containing a neutral gelatin (0.01%), sodium citrate (0.02M), mannitol (0.5%) and sodium chloride (0.05M). The resulting monoclonal antibody solution was then put in 10 ml-volume glass vials (Iwaki Glass Co.) under a sterilized condition, each in an amount of 1 ml, and frozen therein at −80° C. These were freeze-dried in vacuo. The same amount, as that before freeze-drying, of a distilled water for injection was added to the freeze-dried product so that the product was dissolved. The antigen-binding activity of the monoclonal antibody in the resulting solution was measured. As a result, the freeze-dried monoclonal antibody products were found to have the same antigen-binding activity as that of the samples before being frozen.

Example 8

1 mg/ml, as a final concentration, of the same monoclonal antibody as that used in Example 1 was dissolved in 0.1M phosphate buffer (pH 7.0) containing sodium citrate (0.02M), sodium chloride (0.05M) and mannitol (0.5%). The resulting monoclonal antibody solution was then put in glass vials and frozen therein at −80° C. These were freeze-dried in vacuo. The same amount, as that before freeze-drying, of a distilled water for injection was added to the freeze-dried product so that the product was dissolved. The antigen-binding activity of the monoclonal antibody in the resulting solution was measured in the same manner as in Example 1. As a result, the freeze-dried monoclonal antibody products were found to have the same antigen-binding activity as that of the samples before being frozen.

Example 9

Cells of human-human hybridoma MP5121 (FERM BP-2270) producing a human IgM reactive to Group A serotype Pseudomonas aeruginosa, which had been produced by cell fusion, were cultured, and the monoclonal antibody was purified from the culture supernatant in the same manner as in Example 1. The monoclonal antibody was dissolved in 0.1M phosphate buffer (pH 7.0) containing sodium citrate (0.02M), sodium chloride (0.05M) and mannitol (0.5%), to have a final concentration of 1 mg/ml. The resulting monoclonal antibody solution was then put in glass vials and frozen therein at −80° C. These were freeze-dried in vacuo. The same amount, as that before freeze-drying, of distilled water for injection was added to the freeze-dried product so that the product was dissolved. The antigen-binding activity of the monoclonal antibody in the resulting solution was measured in the same manner as in Example 1, provided that the antigen LPS was extracted from Group A serotype Pseudomonas aerugionsa (ATCC 27577). As a result, the freeze-dried monoclonal antibody products were found to have the same antigen-binding activity as that of the samples before being frozen.

Example 10

Monoclonal antibodies were purified from culture supernatants of cells of human IgM-producing human-human hybridoma MP5097, MP5139, MP5114 and MP5156 (FERM BP-2268, 2272, 2269 2339, respectively), all of which had been produced by cell fusion. These monoclonal antibodies had reactivity with Pseudomonas aeruginosa and were reactive to Groups B, E, G and I serotypes Pseudomonas aeruginosa, respectively. Five kinds of monoclonal antibodies comprising 4 kinds of these monoclonal antibodies and the monoclonal antibody used in Example 9 were dissolved in 0.1M phosphate buffer (pH 7.0) containing sodium citrate (0.02M), sodium chloride (0.05M) and mannitol (0.5%), each in an amount, as a final concentration, of 5 mg/ml. These monoclonal antibody solutions were put in glass vials and frozen therein at −80° C. These were freeze-dried in vacuo. The same amount, as that before freeze-drying, of a distilled water for injection was added to each of the freeze-dried products so that each product was dissolved. The antigen-binding activity of each of the monoclonal antibodies in the resulting solutions was measured in the same manner as in Example 1, provided that as the antigen to each antibody, used were LPSs as extracted from ATCC 27577 (to Group A serotype), ATCC 27578 (to Group B serotype), ATCC 27581 (to Group E serotype), ATCC 27584 (to Group G serotype) and ATCC 27586 (to Group I serotype), respectively. As a result, the freeze-dried monoclonal antibody products were found to have the same antigen-binding activity to the five Pseudomonas aeruginosa LPSs of different serotypes, respectively, as that of the samples before being frozen.

In accordance with the present invention characterized by addition of gelatin or carboxylic acid or its salt to a monoclonal antibody-containing solution to be freeze-dried, denaturation of a monoclonal antibody during freeze-drying can be prevented so that a monoclonal antibody-containing freeze-dried preparation having a stable antigen-binding activity can be provided. The present invention may be applied to a monoclonal antibody of any immunoglobulin class, including IgG, IgM, IgA and IgE. Especially, it can be applied to unstable IgM. The present invention may be well applied to any human-derived, mouse-derived and rat-derived monoclonal antibodies. Various numbers and kinds of monoclonal antibodies may be contained in the freeze-dried preparation of the present invention.

The monoclonal antibody-containing freeze-dried preparation of the present invention may be used, like other immunoglobulin-preparations, as an adminiculum for immunoauxotherapy for prophylaxis and treatment of bacterial infectious diseases and viral infectious diseases.

The following deposits were made under the terms of the Budapest Treaty on the International Recognition of the Deposit of Microorganisms for the Purposes of Patent Procedure at the Fermentation Research Institute, Agency of Industrial Science and Technology, 1-3, Higashi 1-chome, Tsukuba-shi, Tbaraki-ken, 305, Japan:

| Depositor's Designation | Date of Deposit | FERM Deposit Number |
|---|---|---|
| MP5038 | Dec. 7, 1989 | BP-1596 |
| MP5097 | Feb. 7, 1989 | BP-2268 |
| MP5139 | Feb. 7, 1989 | BP-2272 |
| MP5114 | Feb. 7, 1989 | BP-2269 |
| MP5156 | Mar. 16, 1989 | BP-2339 |
| MP5121 | Feb. 7, 1989 | BP-2270 |

We claim:

1. A freeze-dried preparation which is prepared by freeze-drying a solution comprising a human monoclonal antibody, gelatin and carboxylic acid or its salt having a pH of from 6.1 to 8.1, the gelatin and carboxylic acid or its salt preventing decrease of antigen binding activity owing to denaturation.

2. The preparation as claimed in claim 1, in which the carboxylic acid is citric acid.

3. The preparation as claimed in claim 1, in which the human monoclonal antibody is one having immunoaglobulin class of IgM.

4. The preparation as claimed in claim 1, in which the gelatin is a neutral gelatin or an acidic gelatin.

5. The preparation as claimed in claim 1, which contains plural human monoclonal antibodies.

* * * * *